US00PP29499P3

(12) United States Plant Patent
Vanlancker

(10) Patent No.: US PP29,499 P3
(45) Date of Patent: Jul. 10, 2018

(54) ***SALVIA* PLANT NAMED 'JEREMY'**

(50) Latin Name: *Salvia microphylla Kunth*
Varietal Denomination: JEREMY

(71) Applicant: Marc Vanlancker, Oudenaarde (BE)

(72) Inventor: Marc Vanlancker, Oudenaarde (BE)

( * ) Notice: Subject to any disclaimer, the term of this patent is extended or adjusted under 35 U.S.C. 154(b) by 0 days.

(21) Appl. No.: 15/731,747

(22) Filed: Jul. 27, 2017

(65) Prior Publication Data

US 2018/0054947 P1 Feb. 22, 2018

(51) Int. Cl.
*A01H 5/02* (2018.01)
*A61K 36/537* (2006.01)

(52) U.S. Cl.
USPC ..... Plt./475
CPC ..... *A01H 5/02* (2013.01); *A61K 36/537* (2013.01)

(58) Field of Classification Search
USPC ..... Plt./475
See application file for complete search history.

(56) References Cited

PUBLICATIONS

PLUTO Plant Variety Database Dec. 4, 2018. p. 1.*

* cited by examiner

*Primary Examiner* — Annette H Para
(74) *Attorney, Agent, or Firm* — Samuel R. McCoy, Jr.

(57) ABSTRACT

'JEREMY' is a new and distinctive variety of *Salvia* which is characterized by a broad, spreading growth habit, an obovate plant form, dark green foliage with greyed-purple venation and petioles, an abundance of pink and white bicolored labiate flowers borne on terminal verticillaster inflorescences, and a floriferous flowering habit. The new variety propagates successfully by stem cuttings and has shown to be uniform and stable in the resulting generations from asexual propagation.

3 Drawing Sheets

Latin name of the genus and species: The Latin name of the genus and species of the novel variety disclosed herein is *Salvia microphylla* Kunth.

Variety denomination: The inventive variety of *Salvia* disclosed herein has been given the variety denomination 'JEREMY'.

CROSS REFERENCE TO RELATED APPLICATIONS

This application claims priority to the Community Plant Variety Rights application number 2016/2012, filed Aug. 17, 2016, which is herein incorporated by reference.

BACKGROUND OF THE INVENTION

Parentage: 'JEREMY' is a seedling selection resulting from the self-pollination of *Salvia microphylla* 'Hot Lips' at a commercial nursery in Oudenaarde, Belgium, in June of 2015. Seed from said cross was harvested, then germinated, and the resulting seedlings were grown to a mature size in order to evaluate for desirable commercial characteristics. Stem cuttings from one candidate plant which exhibited a unique flower color were rooted and grown to a mature size. In September of 2016, the inventor selected the new *Salvia* cultivar from the cutting grown candidates due to the stability of the unique bloom habit. This new and distinctive cultivar was given the name 'JEREMY'.

Asexual Reproduction: Asexual reproduction of 'JEREMY' was first accomplished in September of 2016 by rooting softwood stem cuttings at a commercial greenhouse in Oudenaarde, Belgium. Three successive generations have shown that the unique features of the instant cultivar are stable and reproduce true to type.

SUMMARY OF THE INVENTION

The cultivar 'JEREMY' has not been observed under all possible environmental conditions and the phenotype may vary somewhat with variations in the instant environment such as temperature, day length, and light intensity, without, however, any variance in genotype. The following traits have been repeatedly observed and represent the distinguishing characteristics of the new *Salvia* cultivar, 'JEREMY'.

1. *Salvia* 'JEREMY' exhibits a broad, spreading growth habit and an obovate plant form; and
2. *Salvia* 'JEREMY' exhibits dark green foliage with greyed-purple venation and petioles; and
3. *Salvia* 'JEREMY' exhibits an abundance of pink and white bicolored labiate flowers borne on terminal verticillaster inflorescences; and
4. *Salvia* 'JEREMY' exhibits a floriferous flowering habit.

BOTANICAL DESCRIPTION OF THE PLANT

Figure 1:
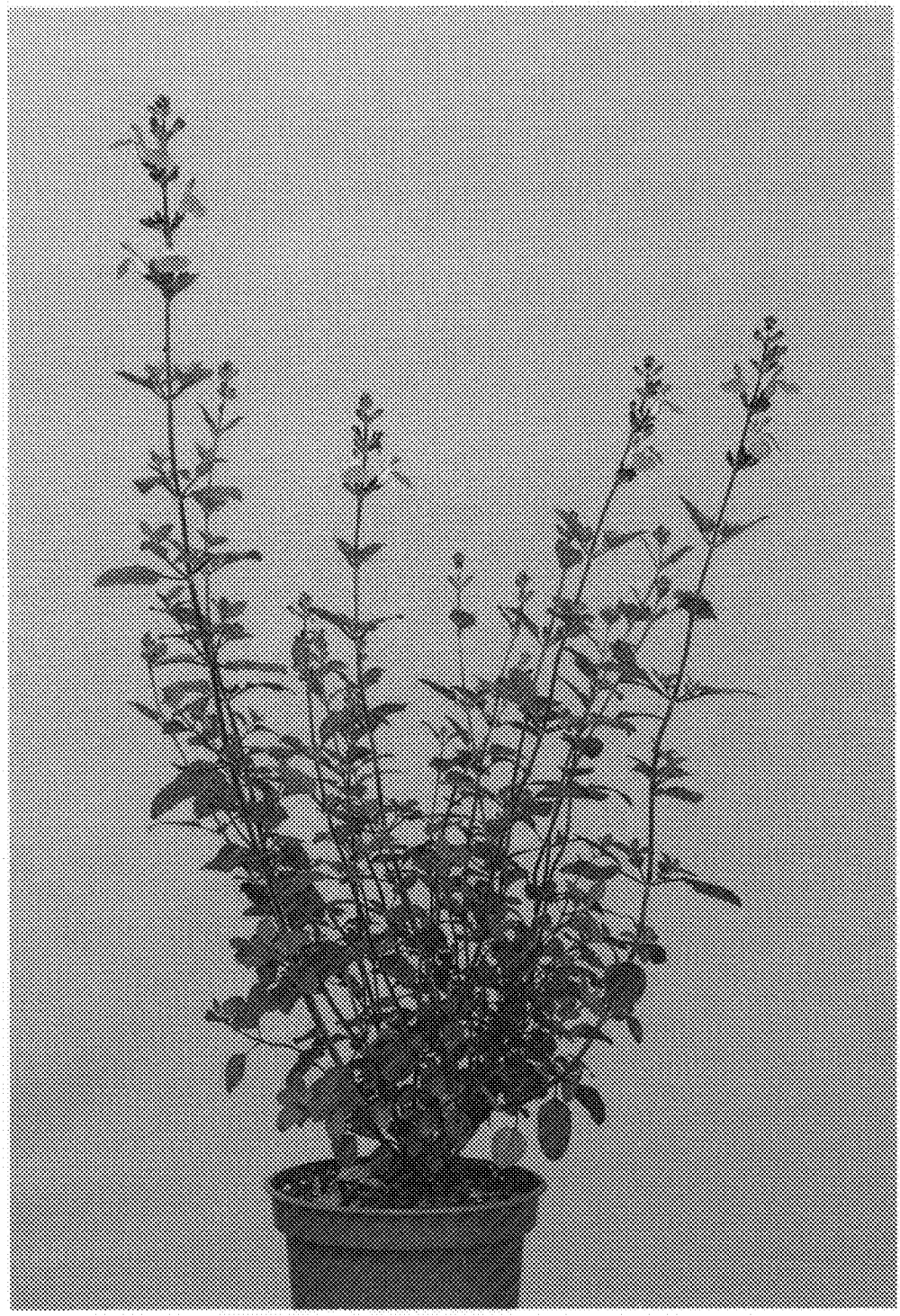
FIG. 1 shows, as nearly true as it is reasonably possible to make the same in color illustrations of this type, an exemplary 'JEREMY' plant at approximately 10 week old, potted into an 18 cm nursery pot, grown in a greenhouse in Oudenaarde, Belgium.
Figure 2:
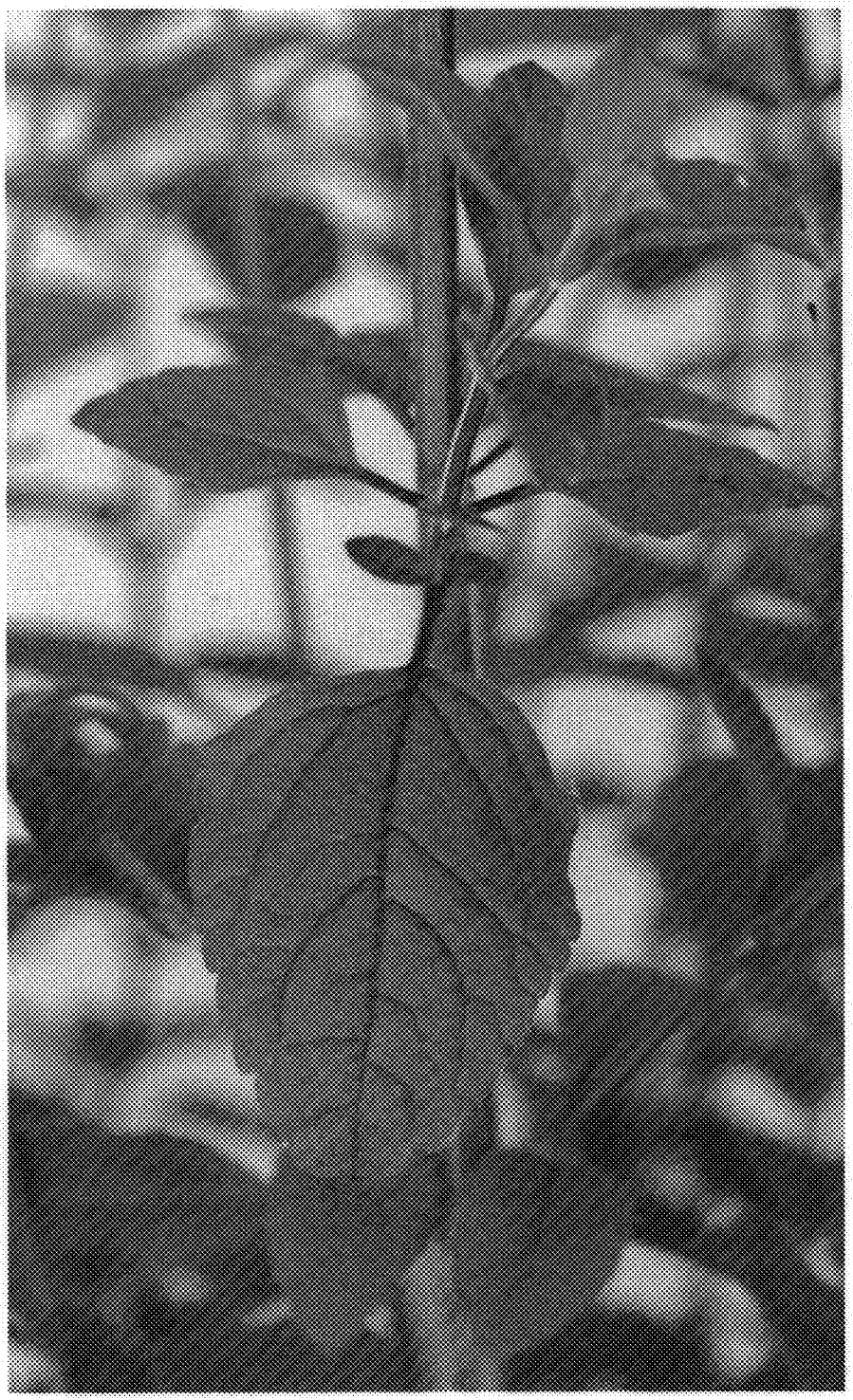
FIG. 2 shows, as nearly true as it is reasonably possible to make the same in color illustrations of this type, the typical foliage of the plant in FIG. 1.
Figure 3:
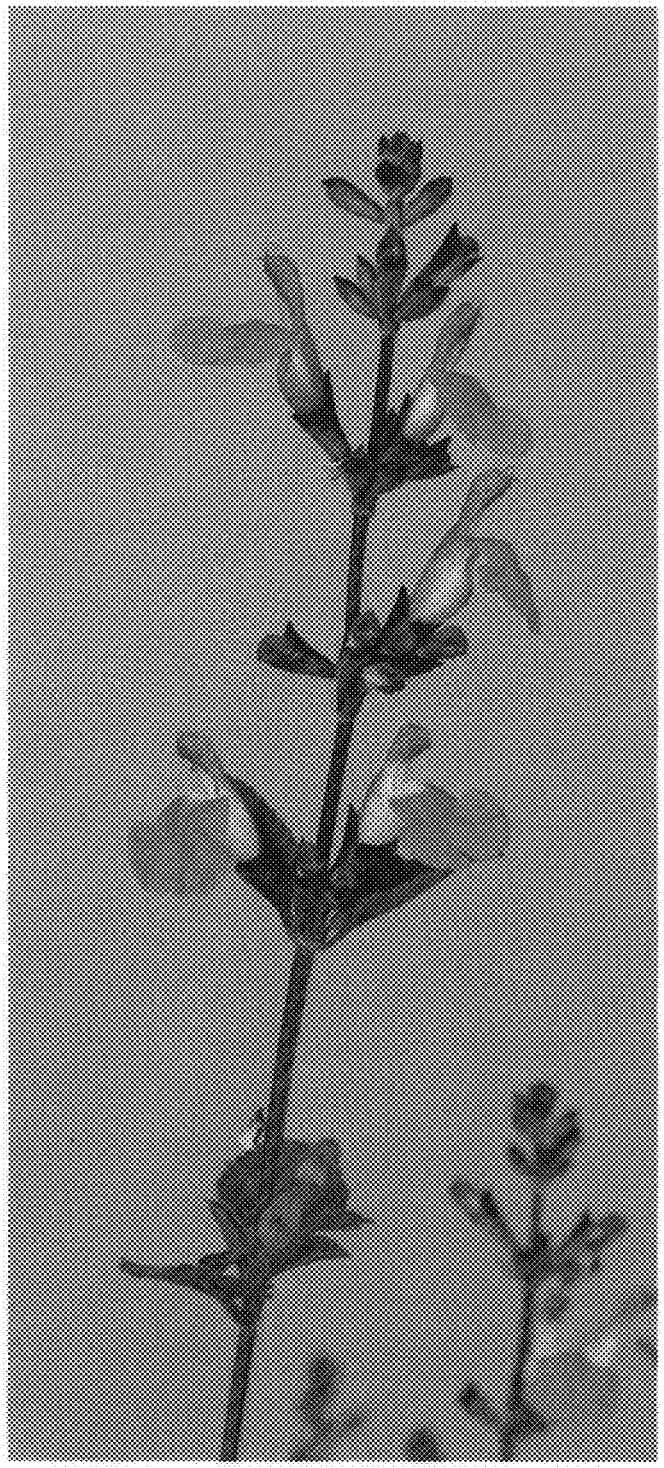
FIG. 3 shows, as nearly true as it is reasonably possible to make the same in color illustrations of this type, the typical flowers of the plant in FIG. 1.

The following is a detailed botanical description of a new and distinct variety of *Salvia* known as 'JEREMY', based upon observations of 3 month old plants in 20 cm nursery containers, grown outdoors in Oudenaarde, Belgium. Plants were grown using conventional field production protocols for *Salvia* plants which consisted of regular drip irrigation and fertilizer applications. No pest or disease control measures were utilized in production. Temperatures ranged between 18 to 30 degrees Celsius during the day and 8 to 15 degrees Celsius at night. Plants were produced with full sun exposure and no photoperiodic treatments or artificial light was given to the plants. Observation data was recorded in May of 2017.

Those skilled in the art will appreciate that certain characteristics will vary with older or, conversely, with younger plants. 'JEREMY' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 edition.

A botanical description of 'JEREMY' and comparisons with the parent and most similar variety of common knowledge are provided below.

General plant description:

*Growth habit*.—A broad, spreading perennial subshrub.

*Plant form*.—Obovate.

*Height*.—53.5 cm to the top of the foliar plane; 58.3 cm to the top of the floral plane.

*Spread*.—40.8 cm.

*Plant vigor*.—Moderate.

*Growth rate*.—Moderate.

*Propagation*.—Softwood stem cuttings; rooting is initiated in approximately 10 days when grown in a greenhouse with an ambient average temperature of 18 degrees Celsius.

*Time to produce a finished plant*.—Approximately 12 weeks are required to produce a marketable finished plant in a 13 cm pot.

*Pest resistance and susceptibility*.—Not any more or less tolerant or susceptible to pests or diseases known to effect *Salvia*.

*Environmental tolerances*.—Adapt to, at least, USDA Zones 8 to 13 and temperatures ranging from 5 degrees Celsius to 40 degrees Celsius; moderate tolerance to rain; moderate tolerance to wind.

Root system: Thin, fibrous, and freely branched.

Stem:

*Branching habit*.—Basally branching main stems growing from a caudex; freely branching with lateral branches. Stems and branches emit a pleasant fragrance when touched. Pinching isn't required but will improve branching.

*Number of primary (main) stems per plant*.—2.

*Number of secondary (lateral) branches per plant*.—31.

*Appearance and shape*.—Quandrangulate.

*Lateral branch length*.—34.1 cm.

*Lateral branch diameter*.—0.25 cm.

*Internode length*.—6.0 cm.

*Luster*.—Very slightly glossy.

*Aspect*.—Main stems are upright; lateral branches are at an average angle of 30 degrees to the main stems (varying between 20 and 40 degrees).

*Strength*.—Moderately strong.

*Color, juvenile*.—Yellow-green, nearest RHS 144C.

*Color, mature*.—Yellow-green, nearest to in between RHS 146B and 146C; upper surfaces where exposed to sunlight are suffused with a mixture of greyed-purple, nearest to RHS 183A, and brown, in between RHS 200C and 200D.

*Color of oldest stems*.—A mixture of greyed-green, nearest to RHS 197A, and grey-brown, nearest to RHS N199A.

*Color at internodes*.—Yellow-green, nearest RHS 146C.

*Pubescence*.—Moderately pubescent; very short, soft hairs with an average length of 0.05 cm and colored white, RHS NN155D.

*Stem luster*.—Moderately glossy.

Foliage:

*Arrangement*.—Opposite.

*Attachment*.—Petiolate.

*Division*.—Simple.

*Quantity*.—Average of 12 leaves per lateral branch.

*Lamina*.—Dimensions — 3.7 cm long and 2.5 cm wide, on average. Shape — Ovate. Aspect — Flat to involute and slightly reflexed. Apex — Obtuse to bluntly acute. Base — Short acute. Margin — Crenate; not undulated. Pubescence and luster of adaxial surface — Moderately pubescent, with soft hairs of average length of 0.03 cm and colored white, nearest to RHS NN155D; very slightly glossy. Pubescence and luster of abaxial surface — Sparsely pubescent, with soft hairs of an average length of 0.02 cm and colored white, nearest to RHS NN155D; matte. Color — Juvenile foliage, adaxial surface — Green, nearest to RHS 143A. Juvenile foliage, abaxial surface — Green, nearest to RHS 138B. Mature foliage, adaxial surface — Green, nearest to RHS 137A. Mature foliage, abaxial surface — In between green, RHS 138A, and yellow-green, RHS 147B. Venation — Pattern — Pinnate. Venation color, adaxial surface — Green, nearest to RHS 137A, becoming greyed-purple as leaves age, RHS N186C. Venation color, abaxial surface — Yellow-green, nearest to RHS 147D, becoming greyed-purple as leaves age, in between RHS 186A and 186B.

*Petiole*.—Length — 1.6 cm. Width — 0.15 cm. Texture — Both the upper and lower surfaces are sparsely pubescent with soft hairs of an average length of 0.02 cm and colored white, nearest to RHS NN155D. Luster — The upper surface is moderately glossy; lower surface is slightly glossy. Strength — Moderately strong. Color, adaxial surface — Brown, in between RHS 200B and 200C, with a greyed-purple main vein, nearest to RHS 186C. Color, abaxial surface — Yellow-green, nearest to RHS 146D.

Inflorescence:

*Type*.—Terminal verticillaster with individual flowers in whorls.

*Natural flowering season*.—Late spring into summer in Oudenaarde, Belgium.

*Time to flower*.—Approximately 10 weeks after flowering.

*Flowering habit*.—Freely flowering.

*Dimensions*.—11.8 cm high, not including peduncle, and 4.2 cm in diameter.

*Quantity of inflorescence per plant*.—15, on average.

*Quantity of flowers per inflorescence*.—30 flowers and buds, on average.

*Attitude*.—Upright; near 0 degrees from vertical.

*Peduncles*.—Length — Average of 11.0 cm. Diameter — Average of 0.175 cm. Attitude — Upright. Strength — Moderately strong. Texture — Moderately pubescent; short, soft hairs with an average length of 0.03 cm and colored white, nearest to RHS NN155D. Luster — Matte. Color — Yellow-green, nearest to in between RHS 146A and 146B.

Flower buds:

*Shape*.—Oblanceolate.

*Length*.—Average of 1.1 cm.

*Diameter*.—Average of 0.35 cm.

*Texture*.—Densely pubescent; very short hairs with an average length of 0.02 cm and colored white, nearest to RHS NN155D.

*Luster*.—Matte.

*Color*.—Upper side is brown, slightly darker than RHS 200A; under side is yellow-green, nearest to RHS 145A; emerging petals at the apex are red-purple, in between RHS 59A and 59B.

Flower:

*Flowering habit*.—Freely flowering.

*Shape*.—Labiate.

*Flower vertical height*.—2.1 cm.

*Flower diameter*.—1.6 cm.

*Flower length*.—3.2 cm.

*Floral throat diameter*.—0.3 cm.

*Floral throat texture*.—Glabrous; smooth.

*Diameter of floral tube*.—Tube flattened; vertical height is 0.7 cm and the horizontal width is 0.3 cm.

*Length of floral tube*.—1.9 cm.

*Floral tube texture*.—Glabrous; smooth.

*Aspect*.—Flowers are outward facing.

*Fragrance*.—Non-fragrant.

*Lastingness*.—Approximately 7 days.

*Persistent*.—Self-cleaning.

*Pedicels*.—Dimensions — 0.45 cm long and 0.1 cm in diameter. Aspect — Upward; approximately 10 degrees to the peduncle axis. Strength — Moderately strong. Texture — Moderately pubescent; short, soft hairs with an average length of 0.3 cm and colored white, nearest to RHS NN155D. Luster — Matte. Color — Yellow-green, nearest to in between RHS 146A and 146B.

*Petals*.—Quantity of petals — 2. Arrangement — Labiate; one upper lip and one lower lip which are fused at the proximal half of the petals. Shape of petal lobes — Upper lip is elliptic; lower lip is spatulate. Dimensions, free portion of the upper petal — 1.1 cm long and 0.3 cm wide. Dimensions, free portion of the lower petal — 1.7 cm long and 1.6 cm wide. Apex — Upper lip is acute; lower lip is cleft into two lobes. Base — Truncate; fused at the base. Margin — Both petal lobs with entire margins; upper petal not undulated and lower petal slightly undulated. Aspect — Moderately reflexed. Pubescence, texture and luster of upper surface — Both petals are moderately pubescent with short hairs with an average length of 0.075 cm and colored red-purple, nearest to RHS 61A, velvety and matte. Pubescence, texture and luster of lower surface — Both petals are glabrous, smooth and matte. Petal lobe color when opening, upper surface — Upper petal — Red-purple, nearest to RHS 62A. Lower petal — Red-purple, in between RHS N57C and 58B. Petal lobe color when opening, lower surface — Upper petal — Red-purple, nearest to RHS 61C. Lower petal — Red-purple, nearest to RHS 63B, and fading lighter towards the floral tube, RHS 63C. Petal lobe color when fully opened, upper surface — Upper petal — Red-purple, nearest to RHS 62C. Lower petal — Red-purple, in between RHS N57C and 58B. Petal lobe color when fully opened, lower surface — Upper petal — Red-purple, nearest to RHS 61C. Lower petal — Red-purple, nearest to RHS 63B, and fading lighter towards the floral tube, RHS 63C. Petal venation — No venation is visible. Floral throat color — White, nearest to RHS NN155D. Floral throat venation color — White, nearest to RHS NN155D. Inner corolla tube color, when fully opened — Upper and lower portions of the tube are red-purple, nearest to RHS 63B; the left and right sides of the tube is white, nearest to RHS NN155D. Outer corolla tube color, when fully opened — Upper and lower portions of the tube are red-purple, nearest to RHS N57C; the left and right sides of the tube is white, nearest to RHS NN155D. Floral tube venation color — No veins are visible.

*Calyx*.—Shape — Campanulate. Length — 1.1 cm. Diameter — Flattened; average horizontal width is 0.3 cm and the height is 0.7 cm. Sepals — Length — 1.1 cm. Width — 0.6 cm, but folded so appears narrower. Arrangement — Campanulate; the flower 72.5 percent of the sepals are fused. Quantity — 2. Shape — Both sepals are narrow oblanceolate. Apex — Upper sepal is acute; lower sepal is cleft. Base — Fused. Sepal lobe margin — Both sepals are entire; not undulated. Pubescence, texture and luster, upper surface — Both sepals are smooth, glabrous, and matte. Pubescence, texture and luster, lower surface — Both sepals are densely pubescent with very short hairs with an average length of 0.2 cm and colored white, nearest to RHS NN155D; slightly glossy. Color when opening, upper surface — Both sepals are yellow-green, nearest to RHS 144B; apex is yellow-green, nearest to RHS 147A. Color when opening, lower surface — Upper sepal — Brown, slightly darker than RHS 200A. Lower sepal — Yellow-green, nearest to RHS 145A. Color when fully opened, upper surface — Both sepals are yellow-green, nearest to RHS 144A; apex is yellow-green, nearest to RHS 147A. Color when fully opened, lower surface — Upper sepal — Nearest to a mixture of brown, RHS 200A, and black, RHS 203A. Lower sepal — Yellow-green, nearest to RHS 145A.

Reproductive organs:

*Stamens*.—Quantity — 2. Anthers — Attachment — Basifixed. Shape — Elliptic. Dimensions — Approximately 0.5 cm long and 0.05 cm wide. Color — Yellow-orange, nearest to RHS 22A. Filaments — Length — 0.5 cm, on average. Color — White, nearest to RHS NN155D. Pollen, amount — Moderately abundant. Pollen color — Yellow-orange, nearest to RHS 14A.

*Pistil*.—Quantity — 1. Length — 2.9 cm. Style — Length — 2.6 cm. Color — White, nearest to RHS NN155D, and fading to red-purple towards the distal end, nearest to in between RHS 72B and 72C. Stigma — Shape — Cleft; decurrent. Length — 0.3 cm. Diameter — 0.4 cm. Color — Red-purple, nearest to RHS 72B. Ovary color — Yellow-green, nearest to in between RHS 150C and 150D.

Seed and fruit: No fruit or seeds have been detected to date.

Comparisons with the parent plants and most similar variety of common knowledge: Plants of the new cultivar 'JEREMY' differ from its parent, *Salvia microphylla* 'Hot Lips' (not patented), by the characteristics described in Chart 1.

CHART 1

| Characteristic | 'JEREMY' | 'Hot Lips' |
|---|---|---|
| General coloration of the flower buds prior to opening. | Yellow-green and suffused with brown. | Yellow-green. |

CHART 1-continued

| Characteristic | 'JEREMY' | 'Hot Lips' |
|---|---|---|
| General coloration of the flower at anthesis. | Pink and white. | Red and white. |
| General coloration of the calyx at anthesis. | Dark yellow-green and suffused with a mixture of brown to black. | Lighter yellow-green. |

Plants of the new cultivar 'JEREMY' may be distinguished from its most similar known commercial comparator, *Salvia microphylla* 'Royal Bumble' (not protected), by the characteristics described in Chart 2.

CHART 2

| Characteristic | 'JEREMY' | 'Royal Bumble' |
|---|---|---|
| General coloration of the flower at anthesis. | Pink and white. | Red. |
| General coloration of the peduncle and pedicels. | Dark yellow-green. | Yellow-green and heavily suffused with a mixture of purple and black. |

That which is claimed is:

1. A new and distinct variety of *Salvia microphylla* plant named 'JEREMY', substantially as described and illustrated herein.

* * * * *